(12) United States Patent
Pugh et al.

(10) Patent No.: US 8,969,830 B2
(45) Date of Patent: Mar. 3, 2015

(54) OPHTHALMIC LENS DISINFECTING BASE UNIT WITH PROGRAMMABLE AND COMMUNICATION ELEMENTS

(75) Inventors: Randall B. Pugh, Jacksonville, FL (US); Edward R. Kernick, Jacksonville, FL (US); William Chester Neeley, Melbourne, FL (US); Dwight Abouhalkah, Jacksonville, FL (US); James Daniel Riall, St. Johns, FL (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 0 days.

(21) Appl. No.: 13/312,167

(22) Filed: Dec. 6, 2011

(65) Prior Publication Data

US 2012/0138818 A1    Jun. 7, 2012

Related U.S. Application Data

(63) Continuation-in-part of application No. 12/961,616, filed on Dec. 7, 2010.

(60) Provisional application No. 61/420,955, filed on Dec. 8, 2010.

(51) Int. Cl.
*A61L 2/24* (2006.01)
*A61L 12/06* (2006.01)
*A61L 2/10* (2006.01)

(52) U.S. Cl.
CPC ............. *A61L 12/063* (2013.01); *A61L 2/10* (2013.01); *A61L 2202/14* (2013.01)
USPC ................ 250/455.11; 422/62; 702/182

(58) Field of Classification Search
USPC ..................................... 250/455.11
See application file for complete search history.

(56) References Cited

U.S. PATENT DOCUMENTS

| 3,852,032 | A | | 12/1974 | Urbach |
| 3,978,341 | A | | 8/1976 | Hoell |
| 4,063,890 | A | | 12/1977 | Baron |
| 4,868,397 | A | | 9/1989 | Tittel |
| 5,120,499 | A | | 6/1992 | Baron |
| 5,144,144 | A | | 9/1992 | Borovsky |
| 5,178,173 | A | * | 1/1993 | Erickson et al. .............. 134/184 |
| 5,439,642 | A | | 8/1995 | Hagmann |

(Continued)

FOREIGN PATENT DOCUMENTS

| DE | 3722384 A | 1/1989 |
| JP | 2002126050 A | 5/2002 |

(Continued)

OTHER PUBLICATIONS

Harris, M.G., et al. "Ultraviolet disinfection of contact lenses." *Optometry and Vision Science*, Oct. 1993;70(10): 839-42. Print.

(Continued)

*Primary Examiner* — Phillip A Johnston

(57) ABSTRACT

The present invention provides for a programmable processor in a disinfecting radiation base unit for working in conjunction with a storage case for an ophthalmic lens. The processor is operative via executable software to provide disinfecting radiation base radiation for disinfecting an ophthalmic lens. A disinfecting radiation base unit and storage case may also include sensors for providing data and a digital storage for storing the data.

12 Claims, 6 Drawing Sheets

(56) References Cited

U.S. PATENT DOCUMENTS

| | | | |
|---|---|---|---|
| 5,500,732 | A | 3/1996 | Ebel et al. |
| 5,618,492 | A | 4/1997 | Auten |
| 6,030,554 | A | 2/2000 | Ichihara |
| 6,461,568 | B1 * | 10/2002 | Eckhardt .................. 422/24 |
| 6,566,659 | B1 | 5/2003 | Clark |
| 6,592,816 | B1 * | 7/2003 | Ebel et al. ............... 422/62 |
| 6,790,409 | B1 | 9/2004 | Nakamura |
| 7,217,936 | B2 | 5/2007 | Ressler |
| 7,242,997 | B2 | 7/2007 | Geng |
| 7,879,288 | B2 | 2/2011 | Brown-Skrobot |
| 8,494,908 | B2 | 7/2013 | Herwig et al. |
| 2002/0026768 | A1 | 3/2002 | Duncan et al. |
| 2004/0234569 | A1 | 11/2004 | Nakada |
| 2005/0013729 | A1 | 1/2005 | Brown Skrobot |
| 2005/0028848 | A1 | 2/2005 | Lai |
| 2005/0079096 | A1 * | 4/2005 | Brown-Skrobot et al. ..... 422/24 |
| 2005/0173652 | A1 | 8/2005 | Ressler |
| 2007/0104611 | A1 | 5/2007 | Marmo |
| 2007/0206377 | A1 * | 9/2007 | Borup ..................... 362/156 |
| 2008/0260601 | A1 * | 10/2008 | Lyon ..................... 422/186.3 |
| 2009/0086160 | A1 | 4/2009 | Enns |
| 2009/0274576 | A1 | 11/2009 | Ressler |
| 2010/0141153 | A1 * | 6/2010 | Recker et al. ............ 315/149 |
| 2010/0259719 | A1 | 10/2010 | Sabeta |
| 2010/0320405 | A1 | 12/2010 | Gardner, III |
| 2011/0084834 | A1 * | 4/2011 | Sabeta ..................... 340/540 |
| 2013/0144743 | A1 | 6/2013 | Pugh |

FOREIGN PATENT DOCUMENTS

| | | |
|---|---|---|
| JP | 2003093481 A | 4/2003 |
| WO | WO 2011/146497 A | 11/2011 |
| WO | WO 2011/146505 A | 11/2011 |
| WO | WO 2012/078744 A | 6/2012 |

OTHER PUBLICATIONS

Admoni, M.M., et al. "Disinfection efficacy in an integrated ultraviolet light contact lens care system." *CLAO J.* Oct. 1994; 20(4): 246-8. Print.

Dolman, P.J., et al. "Contact lens disinfection by ultraviolet light." *American Journal of Ophthalmology*, Dec. 15, 1989;108(6):665-9.

"UV Kills These Bugs.", *Review of Optometry*. Dec. 15, 1999 v136 i12 p. 62.

"Device cleans, disinfects soft contact lenses in 15 minutes.", *Ophthalmology Times.*, Apr. 15, 2004 v29 i8 p. 66.

International Search Report PCT/US2013/025064 dated May 8, 2013.

* cited by examiner

OPHTHALMIC LENS DISINFECTING BASE UNIT WITH PROGRAMMABLE AND COMMUNICATION ELEMENTS

RELATED APPLICATIONS

This application claims priority to patent application, U.S. Ser. No. 12/961,616, filed on Dec. 7, 2010 and entitled "OPHTHALMIC LENS DISINFECTING BASE," as a Continuation in Part Application, the contents of which are relied upon and incorporated by reference and also to Provisional Patent Application 61/420,955.

FIELD OF USE

This invention describes a case for storing an ophthalmic lens and, more specifically, in some embodiments, programmable and communication elements of a base capable of receiving and disinfecting a case storing an ophthalmic lens such as a contact lens.

BACKGROUND

It is well known that contact lenses can be used to improve vision. Various contact lenses have been commercially produced for many years. Early designs of contact lenses were fashioned from hard materials. Although these lenses are still currently used in some applications, they are not suitable for all patients due to their poor comfort and relatively low permeability to oxygen. Later developments in the field gave rise to soft contact lenses, based upon hydrogels.

Hydrogel contact lenses are very popular today. These lenses are often more comfortable to wear than contact lenses made of hard materials. Many hydrogel contact lenses may be worn for more than one day. However, a build-up of microbial life and bacteria on the lenses generally makes it desirable to periodically remove the lenses and disinfect them.

Disinfection of contact lenses traditionally entails placing the contact lens in a container or case and subjecting the contact lens to a chemical disinfectant. However, chemical disinfectants are not always as efficacious as may be desired. From time to time, a contact lens with a bacterium, mold, fungus or other type of adverse life form is reinserted into a user's eye with the result being a diseased eye. In addition, disinfecting solutions tend to be expensive and add to the total cost of using contact lenses for vision correction or cosmetic enhancement. New methods and approaches are therefore needed to disinfect contact lenses.

SUMMARY

Accordingly, the present invention includes an ophthalmic lens disinfecting base unit consisting of a lens storage case and the radiation disinfecting base unit. The lens storage case is capable of storing reusable contact lenses and disinfecting the lenses during the storage by receiving disinfecting radiation in a wavelength and intensity suitable to kill unwanted bacteria, viruses, molds, fungi and the like on a contact lens. The radiation disinfecting base unit receives a lens storage case and provides controlled disinfecting radiation in a wavelength and intensity suitable to kill the unwanted bacteria, viruses, molds, fungi and the like on a contact lens and, in some embodiments, on a lens storage case.

In some embodiments, an ophthalmic lens disinfecting unit includes logic to record and analyze data, to control functions of the ophthalmic lens disinfecting unit, and to display relevant user messages. In other embodiments of the present invention, various programming options are available for an ophthalmic lens disinfecting unit. The present invention may, additionally, include communication options.

DETAILED DESCRIPTION OF THE INVENTION

The present invention includes methods and apparatus for storing and analyzing data related to disinfecting an ophthalmic lens, for controlling functions of an ophthalmic lens storage unit, and for displaying relevant user messages. Also included are options for programming an ophthalmic lens storage unit. Further, communication options allow data to be communicated between an ophthalmic lens storage unit and external devices or entities for various purposes.

In the following sections detailed descriptions of embodiments of the invention will be given. The descriptions of both preferred and alternative embodiments are exemplary embodiments only, and it is understood by those skilled in the art that variations, modifications, and alterations may be apparent. It is therefore to be understood that said exemplary embodiments do not limit the scope of the underlying invention.

GLOSSARY

In this description and claims directed to the presented invention, various terms may be used for which the following definitions will apply:

Disinfecting Radiation: as used herein refers to a frequency and intensity of radiation sufficient to diminish the life expectancy of a life form receiving a Disinfecting Radiation Dose.

Disinfecting Radiation Dose: as used herein refers to an amount of radiation to reduce an amount of life by at least two logs on a logarithmic scale and preferably three logs or more, wherein life includes at least bacteria, viruses, molds and fungi.

Lens: refers to any ophthalmic device that resides in or on the eye. These devices can provide optical correction or may be cosmetic. For example, the term lens can refer to a contact lens, intraocular lens, overlay lens, ocular insert, optical insert or other similar device through which vision is corrected or modified, or through which eye physiology is cosmetically enhanced (e.g. iris color) without impeding vision. In some embodiments, the preferred lenses of the invention are soft contact lenses made from silicone elastomers or hydrogels, which include but are not limited to silicone hydrogels, and fluorohydrogels.

Radiation Disinfecting Base Unit: as used herein refers to a device capable of receiving one or more Radiation Disinfecting Storage Cases to provide disinfecting radiation in wavelengths, durations, and intensities suitable to kill unwanted bacteria, viruses, molds, fungi and the like on one or more contact lenses, and in some embodiments, additionally on the surfaces of the disinfecting storage.

Radiation Disinfecting Storage Case: as used herein refers to a lens storage case capable of storing reusable contact lenses and disinfecting the lenses during the storage by receiving disinfecting radiation in a wavelength and intensity suitable to kill unwanted bacteria, viruses, molds, fungi and the like on a contact lens.

Figure 1:
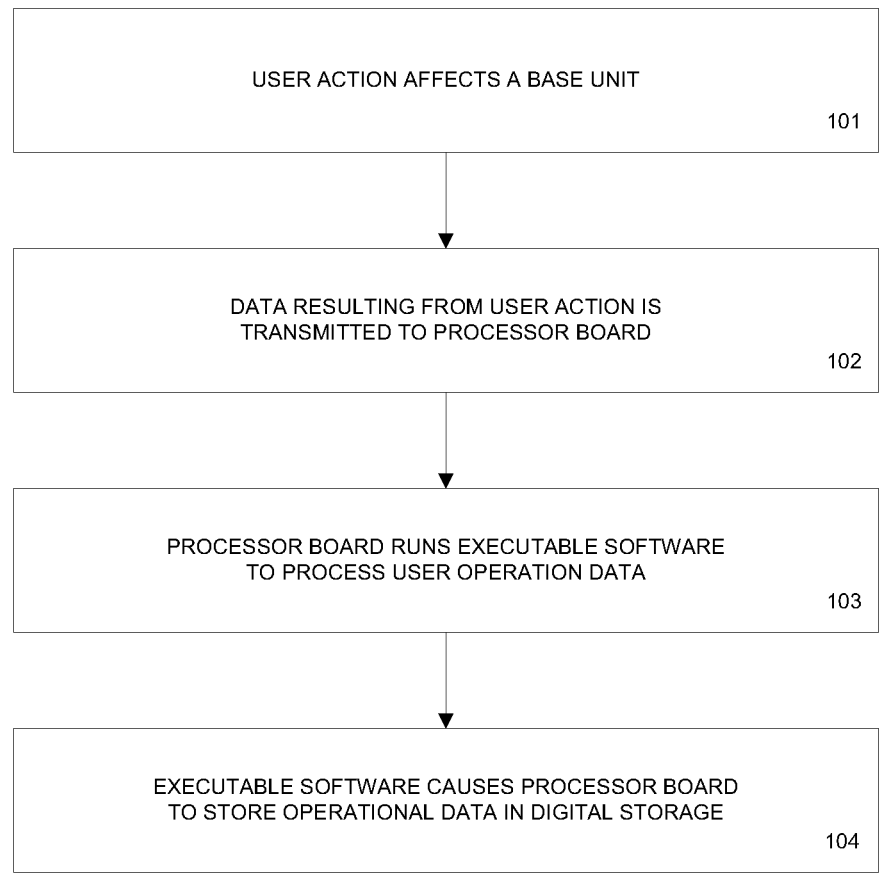
FIG. 1 illustrates method steps for collecting and storing user operation data according to some embodiments of the present invention.

Referring now to FIG. 1, a flowchart illustrates exemplary steps that may be used to implement the present invention. At 101, a user performs an action that affects a radiation disinfecting base unit of an ophthalmic lens disinfecting unit. An action may include, for example, opening a radiation disinfecting base unit, closing a radiation disinfecting base unit, inserting a radiation disinfecting storage case, removing a radiation disinfecting storage case, or pressing a button.

At 102, data resulting from a user action is transmitted to a processor board. Data transmission may include direct electrical connection, such as, for example, via a universal serial buss (USB) or via a wireless transmission, such as for example a radio frequency transmission (RF transmission), Bluetooth, or other mechanism for logical communication.

At 103, a processor board runs executable software to process data resulting from a user action. In some embodiments, executable software resets a lens disinfecting cycle counter after a user presses a reset button on a radiation disinfecting base unit to indicate that fresh lenses are being used. In additional embodiments, executable software resets a radiation disinfecting storage case timer after a user presses a reset button on a radiation disinfecting base unit to indicate a radiation disinfecting storage case has been replaced. Other embodiments include, by way of non-limiting example, executable software incrementing counters for cleaning cycles, timers for lens and storage case usage, and other functions associated with lens and storage case use and disinfection.

At 104, executable software causes a processor board to store data in digital storage. Stored data may include data based on user actions, measurements from sensors, as well as changes resulting from executable software functions such as resetting counters and timers. In some preferred embodiments, stored data includes a date and time associated with a user action or with an executable software action. Data storage may include, for example, user preferred settings, storage in one or more of a historical data log, a current lens data log, and a current radiation disinfecting storage case data log.

Figure 2:
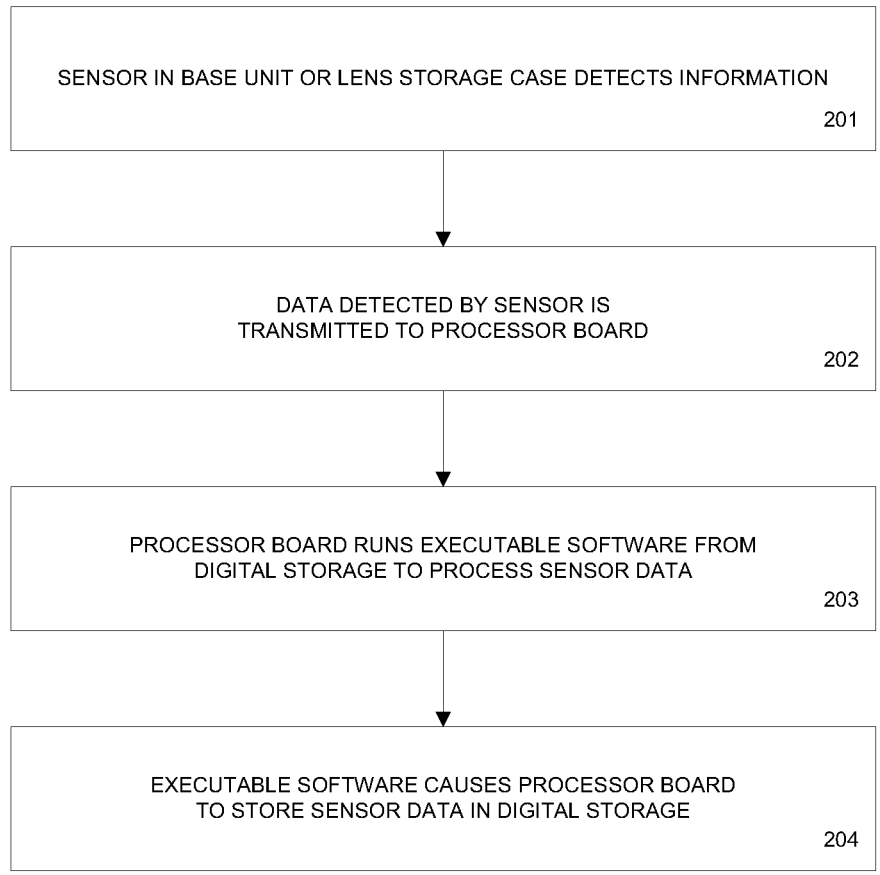
FIG. 2 illustrates method steps for collecting and storing sensor data according to some embodiments of the present invention.

Referring now to FIG. 2, a flowchart illustrates exemplary steps that may be used to implement additional aspects of the present invention. At 201, a sensor in a radiation disinfecting base unit or a radiation disinfecting storage case detects information. A sensor may include, for example, an LED sensor, a charged couple device (CCD) array, a CCD camera, a barcode scanner, or other known sensor such as, for example a device to detect one or both of a an intensity light and a time duration of exposure to a particular wavelength of radiation, temperature of solution in which the lens is stored, pH of solution in which the lens is stored, moisture, amount of protein build up in the lens, or other condition. At 202, sensor data is transmitted to a processor board. Data transmission may include direct electrical connection, radio frequency transmission, or other mechanism for logical communication or transmission. Although the term transmitted is used to describe the transfer of data from the sensor to the processor board, data may be polled from the sensor or otherwise communicated. Each respective transmission medium will be accompanied by an appropriate transmission device. For example, an RF transmission will include a RF transmitter located within the storage case and a RF receiver in the base. Preferred embodiments include both an RF transmitter and receiver in the base and storage case. A direct electrical communication will include a conductive path between the sensor in the storage case and the processor in the base.

At 203, a processor board runs executable software to process sensor data. In some embodiments, sensor data is compared to historical data to determine contact lens or storage case cleanliness. Various embodiments may also include comparison of sensor data to stored baseline data to detect if a radiation disinfecting storage case is present within a radiation disinfecting base unit and to detect if contact lenses are present within a radiation disinfecting storage case. In additional embodiments, sensor data is compared to stored lens profile data, uniquely identifying a contact lens brand. In still other embodiments, sensor data is compared to stored lens data to detect the optical power of each contact lens and thereby identify the right contact lens and the lens contact lens to assist the user of the disinfecting unit.

For example, in some embodiments, a predetermined amount of ultraviolet (UV) radiation may be passed through a contact lens stored in the storage case. One or more sensors may be used to detect amounts of UV radiation passing through one or more portions of the contact lens. A profile may be generated of amounts of radiation passing through the one or more portions. Particular types of lenses will generate identifiable patterns in the profiles. The patterns may be used to identify a type of lens, or even a specific lens.

At 204, executable software causes a processor board to store data in digital storage. Stored data may include data collected by sensors as well as data resulting from executable software analysis such as, for example, a number of days until lenses should be replaced, a number of days until a storage case should be replaced, a percentage of lens opacity indicating lens cleanliness, a percentage of radiation disinfecting storage case opacity indicating radiation disinfecting storage case cleanliness, presence or absence of radiation disinfecting storage case, presence or absence of contact lenses, identified lens brand, and identified lens optical powers. In some preferred embodiments, stored data includes a date and time associated with sensor data or with results from executable software. Data storage may include, for example, storage in one or more of a historical data log, a current lens data log, a current radiation disinfecting storage case data log, and a sensor-specific data log.

Figure 3:
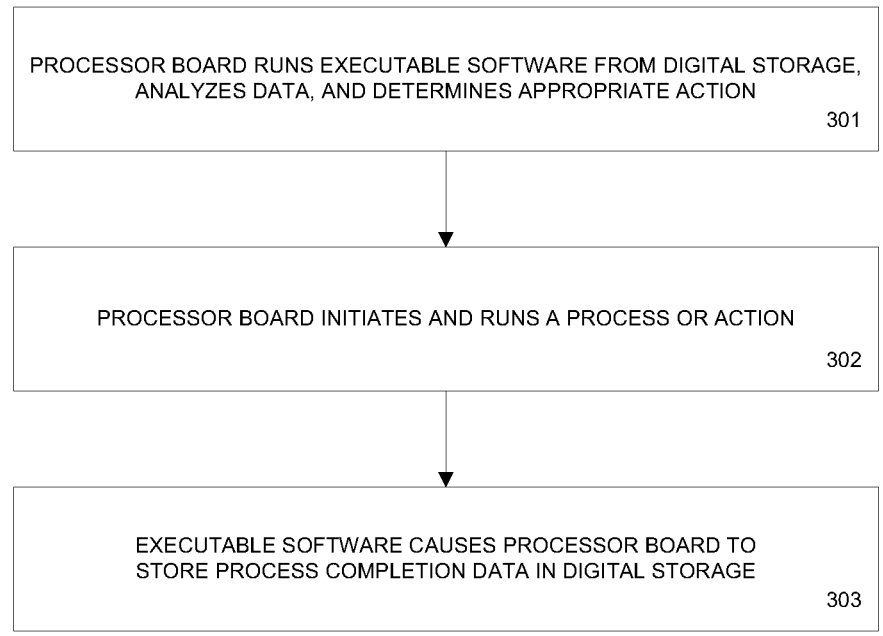
FIG. 3 illustrates method steps for running a process or action, thereby controlling case functions, according to some embodiments of the present invention.

Referring now to FIG. 3, a flowchart illustrates exemplary steps that may be used to implement additional aspects of the present invention. At 301, a processor board runs executable software to analyze previously stored data and determine an appropriate action. In some embodiments of the present invention, executable software analyzes whether a radiation disinfecting base unit has recently been plugged in or been closed. In other embodiments, executable software analyzes stored data to determine when a cleaning cycle should be started. Specific details such as the duration, pattern, and intensity of disinfecting radiation used in a cleaning cycle are calculated or selected in some embodiments of the present invention. In other aspects of the present invention, executable software identifies whether a radiation disinfecting base unit is currently plugged into an external power source.

At 302, a processor board runs a process or action, such as by way of non-limiting example, a radiation disinfecting base case initialization routine and a radiation disinfecting cleaning cycle. Other embodiments include power management actions such as charging a battery in a radiation disinfecting base unit, running the base unit from battery power or running the base unit from direct power.

At 303, executable software causes a processor board to store process completion data in digital storage. Process completion data may include, for example, data related to case initialization processes, including detection of LED strength, detection of presence of radiation disinfecting storage case, detection of contact lenses within radiation disinfecting storage case, and detection of correct contact lens powers in each well of a radiation disinfecting storage case. In other aspects of the present invention, stored data is related to a radiation disinfecting cleaning cycle including duration of radiation, pattern of radiation timing, radiation intensity, and post-disinfection cleanliness data pertaining to contact lenses and radiation disinfecting storage case. In still other embodiments, completion data includes battery charging time, percent battery full, time periods in which base case was operated using a battery and in which base case was operated using direct power. In some preferred embodiments, stored data includes a date and time associated with process completion data. Data storage may include, for example, storage in one or more of a historical data log, a current lens data log, and a current radiation disinfecting storage case data log.

Figure 4:
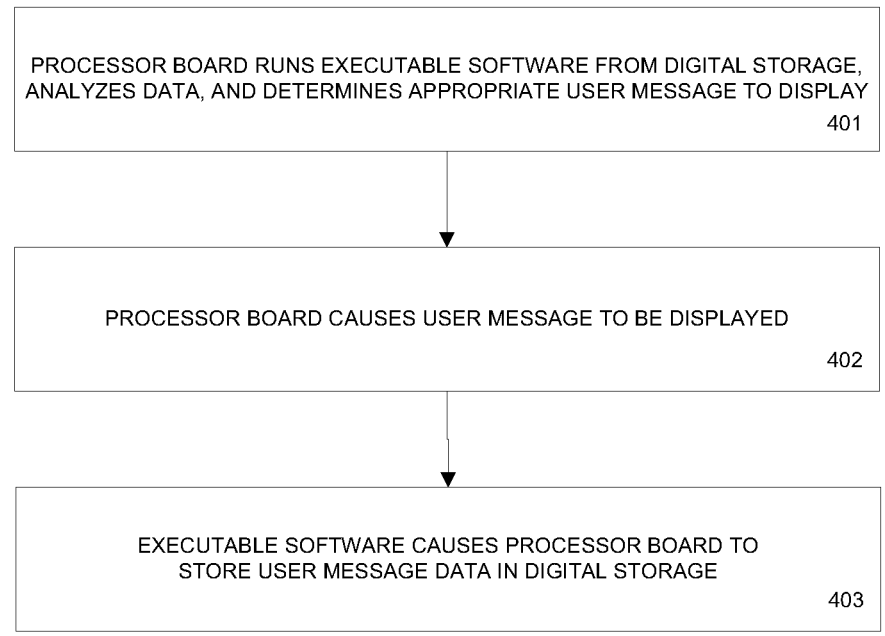
FIG. 4 illustrates method steps for displaying user messages according to some embodiments of the present invention.

Referring now to FIG. 4, a flowchart illustrates exemplary steps that may be used to implement additional aspects of the present invention. At 401, a processor board runs executable software to analyze previously stored data and determines an appropriate user message to be displayed. In some embodiments of the present invention, executable software analyzes, for example, the remaining life of the lens, the need for an appointment with an eye care practitioner, remaining lenses, ordering information and automated ordering, tracking of lenses using a barcode to ensure lenses are not counterfeit lenses, and recommendations of new products for the specific user.

At 402, a processor board causes a user message to be displayed on a message display area of a radiation disinfecting base unit. Some embodiments include messages indicating it is time to insert and disinfect contact lenses, it is time to begin using a new pair of contact lenses, it is time to begin using a new radiation disinfecting storage case, it is time to make an annual appointment with the user's eye care professional, it is time to order new lenses, and new product information specific to the user. In other embodiments, warning messages are displayed, for example, a disinfecting cycle was interrupted, a disinfecting cycle did not complete properly, bar code is not recognized/match the lens per the database and the user should contact a customer service representative, a user has mixed up their right and left contact lenses by placing lenses in the wrong wells of a radiation disinfecting storage case, a user should see their eye care professional soon, as for example, when an unusually high buildup of microbes on lenses has been detected. Still other embodiments include base unit status messages such as, for example, current battery level, battery needs to be recharged, there is not enough battery to complete a cleaning cycle so unit must be plugged in, battery can no longer be recharged so it is time to replace the radiation disinfecting base unit, one or more LEDs are decaying so it is time to replace the radiation disinfecting base unit. Further embodiments include instructional messages such as how to resume a disinfecting cycle, how to restart a disinfecting cycle, how to reprogram a radiation disinfecting base unit, how to store data on a computer or other external device, and how to send data to an eye care professional or other party.

At 403, executable software causes a processor board to store user message data in digital storage. User message data may include, for example, an indication of a specific message displayed and a reason that triggered the specific message. For example, a message to change a contact radiation disinfecting storage case may be triggered because a time limit has been reached or because a sensor detected a change indicator on a radiation disinfecting storage case. In some preferred embodiments, stored data includes a date and time associated with user message display. Data storage may include, for example, storage in one or more of a historical data log, a current lens data log, and a current radiation disinfecting storage case data log.

Figure 5:
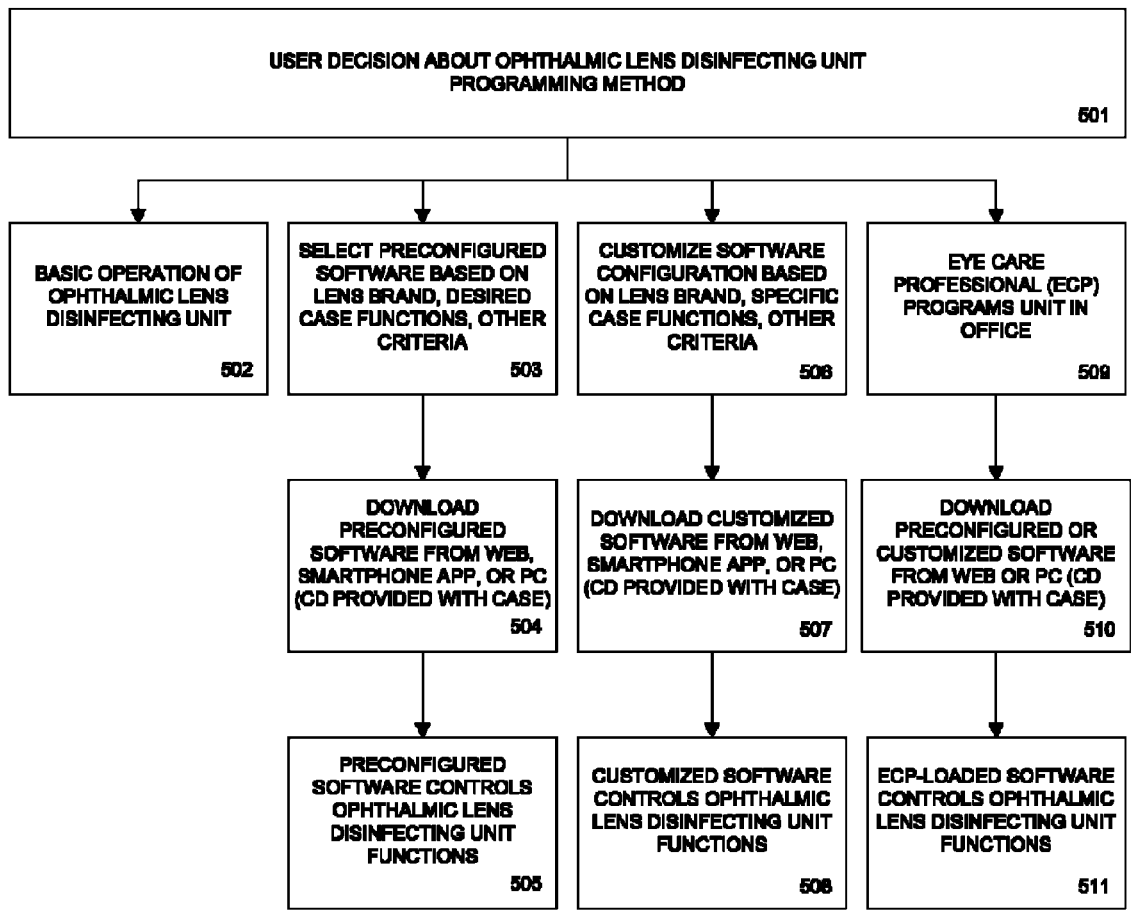
FIG. 5 illustrates method steps for programming an ophthalmic lens disinfecting unit.

Referring now to FIG. 5, a flowchart illustrates exemplary steps that may be used to implement additional aspects of the present invention. At 501, a user determines how to program an ophthalmic lens disinfecting unit by selecting specific setting options. The user decision may be based on information provided with an ophthalmic lens disinfecting unit, information available on a website, information from their eye care professional, information from lens manufacturer or other source. The user decision leads to 502, 503, 506 or 509. A user may download different preconfigured or customized software at any time. A new software download may be desirable if a user's lens brand or lens parameters change, if updated software is available to correct program errors, if the user desires more or less functionality from the ophthalmic lens disinfecting unit, and for other reasons. After loading a preconfigured or customized program, a user may or may not be provided with an option to revert their ophthalmic lens disinfecting unit to its basic operational state.

At 502, a user decides to use only basic functions provided with an ophthalmic lens disinfecting unit. No additional steps, programming, or configuration are necessary to use the unit with base functionality. Basic operation may include, by way of non-limiting example, initialization routine when user closes case, generic radiation disinfecting cycle appropriate for many disposable lenses, and basic user messages.

At 503, a user selects from a limited number of preconfigured software options for an ophthalmic lens disinfecting unit. Preconfigured software may be selected, for example, on the basis of the lens brand worn by the user, on desired case functions, and other criteria. At 504, selected preconfigured software is downloaded to an ophthalmic lens disinfecting unit from a website, a Smartphone application, a PC using a CD provided with an ophthalmic lens disinfecting unit, or other known method of software distribution. At 505, an ophthalmic lens disinfecting unit is controlled using preconfigured software. In addition to the functions available in basic operation, preconfigured software may support, by way of non-limiting example, radiation disinfecting cycles specific to a contact lens brand and wear schedule, counters and reminders based on standard lens wear schedules, ability to later upload data from ophthalmic lens disinfecting unit for analysis, expanded user messages, and other functions.

At 506, a user customizes software configuration for an ophthalmic lens disinfecting unit. Software may be customized, for example, by selecting specific brand and lens parameters worn by a user for each eye, by selecting custom lens wear schedules, by selecting or blocking functions such as counters and reminders, by entering date of last eye exam or lens purchase to enable reminder for subsequent eye exams or lens purchases, by entering a name or other indentifying information, by selecting data communication options, by scanning a bar code in the packaging of the lens to download specific information about the lens, and other functions. At 507, customized software is downloaded to an ophthalmic lens disinfecting unit from a website, a Smartphone application, a PC using a CD provided with an ophthalmic lens disinfecting unit, or other known method of software distribution. At 508, an ophthalmic lens disinfecting unit is controlled using customized software. In addition to the functions available in basic operation, customized software may support, by way of non-limiting example, radiation disinfecting cycles specific to a contact lens brand and parameters worn by a user, counters and reminders based on lens wear schedule indicated by a user, ability to identify wrong contact lens powers in wrong wells of storage case, ability to later upload data from ophthalmic lens disinfecting unit for analysis, customized user messages, display of user name or other identifying information, communication of data to other devices, and other functions.

At 509, an eye care professional (ECP) programs an ophthalmic lens disinfecting unit in the office for a user. An ECP may use preconfigured software as described in the path starting at step 503, or may use customized software configuration as described in the path starting at step 506. At 510, preconfigured or customized software is downloaded to an ophthalmic lens disinfecting unit from a website, a Smartphone application, a PC using a CD provided with an ophthalmic lens disinfecting unit, or other known method of software distribution. At 511, an ophthalmic lens disinfecting unit is controlled using preconfigured software as described previously in step 505, or customized software as described previously in step 508.

Figure 6:
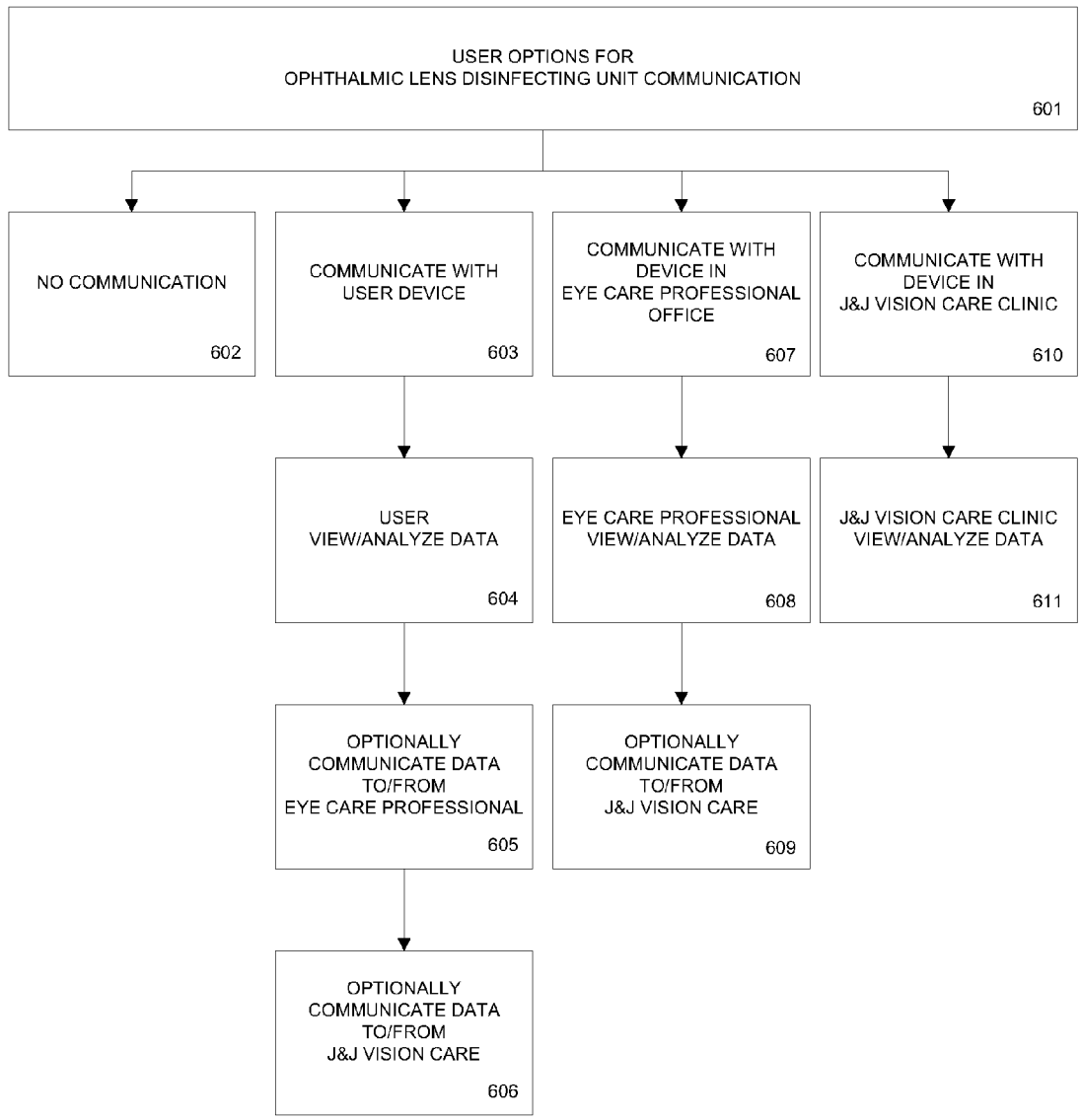
FIG. 6 illustrates method steps for communicating data between an ophthalmic lens disinfecting unit and other devices and entities.

Referring now to FIG. 6, a flowchart illustrates exemplary steps that may be used to implement additional aspects of the present invention. At 601, a user may make a decision about communicating data from an ophthalmic lens disinfecting unit. Alternatively, a default communication may be implemented The user decision may be based, for example, on information provided with an ophthalmic lens disinfecting unit, information available on a website, information from their eye care professional, or other source. One or both of a user decision and a default communication mode eventually can lead to 602, 603, 607 or 610.

At 602, a user decides to use an ophthalmic lens disinfecting unit in a standalone manner. In various implementations, data may be stored for subsequent analysis or simply not recorded.

At 603, a user enables communication between an ophthalmic lens disinfecting unit and a user device such as a PC, Smartphone, or other device capable of receiving ophthalmic lens disinfecting unit data. In some preferred embodiments, an ophthalmic lens disinfecting unit application available via a PC, Smartphone or other device facilitates the sharing of data. An ophthalmic lens disinfecting unit application may be a standalone application running on a computing device, may be an application available on a website accessed using a computing device, or may be a distributed application with functions running on a both standalone computing device and a website.

At 604, an ophthalmic lens disinfecting unit application is used to view and analyze ophthalmic lens disinfecting unit data. In some embodiments, data includes text, charts, graphs, and other representations. Data may include, by way of non-limiting example, contact lens brand and parameters, contact lens wear schedules, user specific information, cleaning cycle details, contact lens cleanliness data, contact lens and radiation disinfecting storage case replacement history, number of days until recommended contact lens replacement, number of days until recommended radiation disinfecting storage case replacement. Other embodiments include ophthalmic lens disinfecting unit diagnostic information, such as, for example, battery information, LED information, sensor information, and communication details.

At 605, a user makes a decision to send ophthalmic lens disinfecting unit data to an eye care professional. In some preferred embodiments, an ophthalmic lens disinfecting unit application facilitates the sharing of data with an eye care professional using known data transmission methods, such as, for example, sending an email containing text information, sending an email containing a data file, making a file or data available on a website to which the eye care professional has access, or other means. Ophthalmic lens disinfecting unit data shared with an eye care professional may include, by way of non-limiting example, contact lens brand and parameters, contact lens wear schedules, user specific information, cleaning cycle details, contact lens cleanliness data, contact lens and radiation disinfecting storage case replacement history, number of days until recommended contact lens replacement, number of days until recommended radiation disinfecting storage case replacement. Other embodiments may include the sharing of ophthalmic lens disinfecting unit diagnostic information, such as, for example, battery information, LED information, sensor information, and communication details. Shared data may be in the form of text, charts, graphs, and other representations. In another aspect, in some embodiments, an eye care professional may also be capable of transmitting messages and data to a user's ophthalmic lens disinfecting unit application, where it may be viewed in the application or may be transmitted to an ophthalmic lens disinfecting unit and displayed on the display area. Eye care professional messages and data may include, for example, eye exam reminders, contact lens purchase reminders, sale information, ordering information, or other information.

At 606, a user makes a decision to send ophthalmic lens disinfecting unit data to a contact lens manufacturer or other provider of contact lenses. In some preferred embodiments, an ophthalmic lens disinfecting unit application facilitates the sharing of data with a manufacturer or other provider of contact lenses using known data transmission methods, such as, for example, sending an email containing text information, sending an email containing a data file, making a file or data available on a website to which the manufacturer or other provider of contact lenses has access, or other means. Ophthalmic lens disinfecting unit data shared with a manufacturer or other provider of contact lenses may include, by way of non-limiting example, contact lens brand and parameters, contact lens wear schedules, user specific information, cleaning cycle details, contact lens cleanliness data, contact lens and radiation disinfecting storage case replacement history, number of days until recommended contact lens replacement, number of days until recommended radiation disinfecting storage case replacement. Other embodiments may include the sharing of ophthalmic lens disinfecting unit diagnostic information, such as, for example, battery information, LED information, sensor information, and communication details. Shared data may be in the form of text, charts, graphs, and other representations. In another aspect, in some embodiments, a manufacturer or other provider of contact lenses may also be capable of transmitting messages and data to a user's ophthalmic lens disinfecting unit application, where it may be viewed in the application or may be transmitted to an ophthalmic lens disinfecting unit and displayed on the display area. Manufacturer messages and data may include, for example, eye exam reminders, contact lens purchase reminders, ordering information, and interphase for automated ordering, contact lens rebate information, contact lens purchase coupons, or other information.

At 607, a user provides an ophthalmic lens disinfecting unit to an eye care professional, who enables communication from the ophthalmic lens disinfecting unit to a device in the eye care professional office such as a PC, Smartphone, or other device capable of receiving ophthalmic lens disinfecting unit data. In some preferred embodiments, an ophthalmic lens disinfecting unit application available via a PC, Smartphone or other device facilitates the sharing of data. An ophthalmic lens disinfecting unit application may be a standalone application running on a computing device, may be an application available on a website accessed using a computing device, or may be a distributed application with functions running on a both standalone computing device and a website. At 608, an ophthalmic lens disinfecting unit application is used to view and analyze ophthalmic lens disinfecting unit data. In some embodiments, data includes text, charts, graphs, and other representations. Data may include, by way of non-limiting example, contact lens brand and parameters, contact lens wear schedules, user specific information, cleaning cycle details, contact lens cleanliness data, contact lens and radiation disinfecting storage case replacement history, number of days until recommended contact lens replacement, number of days until recommended radiation disinfecting storage case replacement. Other embodiments include ophthalmic lens disinfecting unit diagnostic information, such as, for example, battery information, LED information, sensor information, and communication details. In another aspect, in some embodiments, an eye care professional may also be capable of transmitting messages and data to a user's ophthalmic lens disinfecting unit, where it may be displayed on the display area. Eye care professional messages and data may include, for example, eye exam reminders, contact lens purchase reminders, sale information, or other information.

At 609, an eye care professional makes a decision to send ophthalmic lens disinfecting unit data to a contact lens manufacturer or other provider of contact lenses. In some preferred embodiments, an ophthalmic lens disinfecting unit application facilitates the sharing of data with a manufacturer or other provider of contact lenses using known data transmission methods, such as, for example, sending an email containing text information, sending an email containing a data file, making a file or data available on a website to which the manufacturer or other provider of contact lenses has access, or other means. Ophthalmic lens disinfecting unit data shared with a manufacturer or other provider of contact lenses may include, by way of non-limiting example, contact lens brand and parameters, contact lens wear schedules, user specific information, cleaning cycle details, contact lens cleanliness data, contact lens and radiation disinfecting storage case replacement history, number of days until recommended contact lens replacement, number of days until recommended radiation disinfecting storage case replacement. Other embodiments may include the sharing of ophthalmic lens disinfecting unit diagnostic information, such as, for example, battery information, LED information, sensor information, and communication details. Shared data may be in the form of text, charts, graphs, and other representations.

At 610, a user provides an ophthalmic lens disinfecting unit to a manufacturer or other provider of contact lenses eye care professional, who enables communication from the ophthalmic lens disinfecting unit to a device in the manufacturer office such as a PC, Smartphone, or other device capable of receiving ophthalmic lens disinfecting unit data. In some preferred embodiments, an ophthalmic lens disinfecting unit application available via a PC, Smartphone or other device facilitates the sharing of data. An ophthalmic lens disinfecting unit application may be a standalone application running on a computing device, may be an application available on a website accessed using a computing device, or may be a distributed application with functions running on a both standalone computing device and a website. At 611, an ophthalmic lens disinfecting unit application is used to view and analyze ophthalmic lens disinfecting unit data. In some embodiments, data includes text, charts, graphs and other representations. Data may include, by way of non-limiting example, contact lens brand and parameters, contact lens wear schedules, user specific information, cleaning cycle details, contact lens cleanliness data, contact lens and radiation disinfecting storage case replacement history, number of days until recommended contact lens replacement, number of days until recommended radiation disinfecting storage case replacement. Other embodiments include ophthalmic lens disinfecting unit diagnostic information, such as, for example, battery information, LED information, sensor information, and communication details. In another aspect, in some embodiments, a manufacturer or other provider of contact lenses may also be capable of transmitting messages and data to a user's ophthalmic lens disinfecting unit where it may be displayed on the display area. Manufacturer messages and data may include, for example, eye exam reminders, contact lens purchase reminders, contact lens rebate information, contact lens purchase coupons, or other information.

CONCLUSION

The present invention, as described above and as further defined by the claims below, provides methods for collecting and storing data, controlling case functions, displaying user messages, and programming an ophthalmic lens disinfecting base unit. Further, communication options allow data to be communicated between an ophthalmic lens storage unit and external devices or entities for various purposes.

We claim:
1. A method for disinfecting a contact lens comprising:
providing a disinfecting base unit with programmable elements,
   wherein the base unit comprises a receptacle for receiving an ophthalmic lens storage case, said storage case capable of storing one or more ophthalmic contact lenses in solution;
   performing an action on said base unit, said step of performing an action chosen from:
opening said base unit, closing said base unit, or inserting a storage case into said base unit; said action resulting in the creation of action data in response to the action, wherein a sensing device in the base unit detects the action data;
   transmitting the action data to a processor board;
   processing the action data using executable software, wherein the executable software is included in the processor board;
   storing the action data in digital storage, wherein the storage is caused by the executable software;
   using said data to cause the disinfecting of a contact lens in said base unit;
   wherein a user determines how to program said disinfecting base unit.

2. The method of claim 1 wherein the sensing device measures temperature of the solution in which the lens is stored.

3. The method of claim 1 further comprising the steps of:
running the executable software;
retrieving stored data from digital storage;
analyzing the stored data so as to formulate a responsive action based on the analysis of the stored data;
initiating the responsive action;
completing the responsive action;
populating responsive action data; and
storing the responsive action data in digital storage.

4. The method of claim 3, wherein the responsive action is to display a message on said base unit.

5. The method of claim 3, wherein the responsive action is to initiate disinfecting means on the ophthalmic lens.

6. The method of claim 3, further comprising the steps of:
running the executable software;
retrieving stored data;
initiating logical communication with an external device;
transferring stored data to the external device; and
terminating logical communication with the external device.

7. The method of claim 6 further comprising the steps of:
receiving action data from the external device.

8. The method of claim 6, wherein the communication is wireless.

9. The method of claim 6, wherein the communication occurs through a universal serial bus connection between the processor and the personal processing device.

10. The method of claim 3 further comprising the steps of:
initiating logical communication with a personal processing device;
transferring a specially configured executable software to the processor board, wherein the configuration occurs prior to transfer and sets specific ophthalmic parameters;
overriding a preexisting executable software with the specially configured executable software; and
terminating logical communication with the personal processing device.

11. The method of claim 10, wherein the communication is wireless.

12. The method of claim 10, wherein the communication occurs through a universal serial bus connection between the processor and the personal processing device.

* * * * *